United States Patent

Kleefeld et al.

[11] Patent Number: 5,883,091
[45] Date of Patent: Mar. 16, 1999

[54] 1,3,4-OXADIAZINE DERIVATIVES HAVING A PESTICIDE EFFECT

[75] Inventors: Gerd Kleefeld, Neuss; Johannes Kanellakopulos, Dormagen; Ulrike Wachendorff-Neumann, Neuwied, all of Germany

[73] Assignee: Bayer Aktiengesellschaft, Leverkusen, Germany

[21] Appl. No.: 860,757

[22] PCT Filed: Dec. 4, 1995

[86] PCT No.: PCT/EP95/04760

§ 371 Date: Jun. 6, 1997

§ 102(e) Date: Jun. 6, 1997

[87] PCT Pub. No.: WO96/18624

PCT Pub. Date: Jun. 20, 1996

[30] Foreign Application Priority Data

Dec. 16, 1994 [DE] Germany .......................... 44 44 865.1

[51] Int. Cl.[6] .................. C07D 273/04; C07D 413/04; A01N 43/88
[52] U.S. Cl. .................... 514/229.2; 544/66; 544/69; 514/63; 564/49
[58] Field of Search ............... 544/66; 514/229.2

[56] References Cited

U.S. PATENT DOCUMENTS

| | | | |
|---|---|---|---|
| 3,119,821 | 1/1964 | Trepanier | 544/66 |
| 3,420,825 | 1/1969 | Trepanier | 544/66 |
| 3,420,826 | 1/1969 | Trepanier | 544/66 |
| 4,782,066 | 11/1988 | Dekeyser et al. | 514/229.2 |
| 5,462,938 | 10/1995 | Annus | 544/66 |
| 5,536,720 | 7/1996 | Dekeyser et al. | 514/229.2 |
| 5,677,301 | 10/1997 | Dekeyser et al. | 544/66 |

FOREIGN PATENT DOCUMENTS

| | | |
|---|---|---|
| 461929 | 2/1975 | Russian Federation . |
| 93-22311 | 11/1993 | WIPO . |
| 95-18116 | 7/1995 | WIPO . |

OTHER PUBLICATIONS

Ismail et al Pest. Biochem & Physiol. vol. 47 pp. 1–7, 1993.
Potek Hin, Chem Abstr. vol. 83 p. 858 entry 10171j, 1975.

*Primary Examiner*—Donald G. Daus
*Attorney, Agent, or Firm*—Sprung Kramer Schaefer & Briscoe

[57] ABSTRACT

The invention relates to new 1,3,4-oxadiazine derivatives of the formula (I)

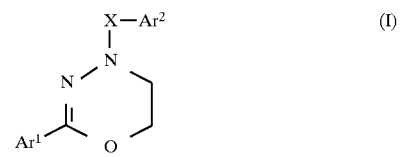

in which

Ar[1] represents in each case optionally substituted aryl or hetaryl,

Ar[2] represents in each case optionally substituted aryl or hetaryl and

X represents the group $-(CHR^1)_m-(CHR^2)_n$ in which
R[1] represents hydrogen or alkyl,
R[2] represents hydrogen or alkyl,
m represents 0 or 1 and
n represents 0 or 1, to a plurality of processes for their preparation, and to their use for combating animal pests.

3 Claims, No Drawings

1,3,4-OXADIAZINE DERIVATIVES HAVING A PESTICIDE EFFECT

The invention relates to new 1,3,4-oxadiazine derivatives, to a plurality of processes for their preparation, and to their use for combating animal pests.

It has already been disclosed that certain 1,3,4-oxadiazine derivatives, such as, for example, 2-(4-brormophenyl)-4-(2-fluoroeth-1-yl)-4H-5,6-dihydro-1,3,-4-oxadiazine have acaricidal properties (cf. Pesticide Biochemistry and Physiology 47, 1–7 (1993)).

However, the level and/or duration of action of these prior-art compounds is not entirely satisfactory in all fields of application, in particular when used against certain or,), anisms or at low rates.

There have now been found new 1,3,4-oxadiazine derivatives of the formula (I)

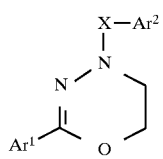

(I)

in which
Ar$^1$ represents in each case optionally substituted aryl or hetaryl,
Ar$^2$ represents in each case optionally substituted aryl or hetaryl and
X represents the group —(CHR$^1$)$_m$—(CHR$^2$)$_n$ in which
R$^1$ represents hydrogen or alkyl,
R$^2$ represents hydrogen or alkyl,
m represents 0 or 1 and
n represents 0 or 1.

Furthermore, it has been found that the new 1,3,4-oxadiazine derivatives of the formula (I) are obtained when
a) acid hydrazides of formula (II)

in which
Ar$^1$, Ar$^2$ and X have the abovementioned meanings, are reacted with ethane derivatives of the formula (III)

in which
Y$^1$ and Y$^2$ are identical or different and represent in each case a leaving group
in the presence of a base and in the presence of a diluent; or
b) acid hydrazides of the formula (IV)

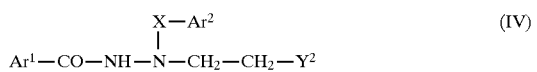

in which
Ar$^1$, Ar$^2$, X and Y$^2$ have the abovementioned meanings, are cyclized, if appropriate in the presence of a catalyst, if appropriate in the presence of a base and if appropriate in the presence of a diluent; or
c) acid hydrazides of the formula (V)

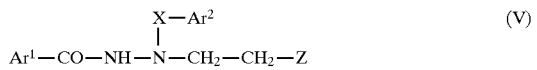

in which
Ar$^1$, Ar$^2$ and X have the abovementioned meanings and

Z represents —OH or —O—COR, where
R represents alkyl
are cyclized in the presence of an acid and if appropriate in the presence of a diluent; or
d) 1,3,4-oxadiazine derivatives of the formula (VI)

(VI)

in which
Ar$^1$ has the abovementioned meanings
are reacted with compounds of the formula (VII)

in which
Ar$^2$, R$^1$, R$^2$, Y$^1$, m and n have the abovementioned meanings, and at least one of the indices m and n represents 1
in the presence of a base and if appropriate in the presence of a diluent; or
e) 1,3,4-oxadiazine derivatives of the formula (Ia)

(Ia)

in which
Ar$^1$ has the abovementioned meanings and
Ar$^3$ represents halogenoaryl or halogenohetaryl are reacted with boronic acids of the formula (VIII)

in which
Ar$^4$ represents optionally substituted aryl
in the presence of a base and in the presence of a diluent.

Furthermore, it has been found that the new 1,3,4-oxadiazine derivatives of the formula (I) are highly suitable for combating animal pests. They are distinguished, in particular, by a potent activity against arthropods.

Surprisingly, the 1,3,4-oxadiazine derivatives of the formula (I) according to the invention display a considerably better activity against animal pests than the prior-art compounds of the most similar constitution, such as, for example, 2-(4-bromophenyl)-4-(2-fluoroethyl-1-yl)-4H-5, 6-dihydro-1,3,4-oxadiazine.

Formula (I) provides a general definition of the compounds according to the invention.

Preferred substituents or ranges of the radicals mentioned in the formula given hereinabove and hereinbelow are illustrated in the following text.

Ar$^1$ preferably represents phenyl which is optionally mono-substituted to pentasubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-haloogenoalkoxy, $C_1$–$C_6$-halogenoalkylthio, nitro and cyano, or represents 5- or 6-membered hetaryl having one or two identical or different hetero atoms from the series consisting of oxygen, sulphur and nitrogen which is optionally monosubstituted to trisubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro and cyano.

$Ar^2$ preferably represents phenyl which is optionally monosubstituted to pentasubstituted by identical or different substituents from the series consisting of halogen, $C_1$–$C_{18}$-alkyl, $C_1$–$C_8$-alkoxy-$C_1$–$C_8$-alkyl, $C_1$–$C_8$-halogenoalkoxy, $C_1$–$C_4$-halogenoalkyl, $C_1$–$C_{18}$-alkoxy which is optionally interrupted by a further 1 to 3 oxygen atoms, $C_1$–$C_{18}$-alkylthio, $C_1$–$C_8$-halogenoalkylthio, cyclohexyl or cyclohexyloxy, each of which is optionally substituted by $C_1$–$C_6$-alkyl, $C_1$–$C_6$-alkoxy, cyclohexyl or phenyl, pyridyloxy which is optionally monosubsutituted or disubstituted by identical or different substituents from the series consisting of halogen, $C_1$–$C_4$-alkyl and $C_1$–$C_4$-halogenoalkyl, and phenyl, benzyl, phenethyl, phenoxy, phenoxymethyl, phenylthio, benzyloxy, phenethyloxy, benzylthio or styryl, each of which is optionally monosubstituted to trisubstituted by identical or different substituents from the series consisting of $C_1$–$C_{12}$-alkyl, halogen, cyano, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–$C_6$-alkoxy-ethylenoxy, $C_1$–$C_6$-alkylthio, $C_1$–$C_6$-halogenoalkylthio and trimethylsilyl, or represents 5- or 6-membered hetaryl having one or two identical or different hetero atoms from the series consisting of oxygen, sulphur and nitrogen which is optionally monosubstituted to trisubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkyl, nitro and cyano.

X preferably represents the group —$(CHR^1)_m$—$(CHR^2)_n$—, in which
$R^1$ represents hydrogen or $C_1$–$C_4$-alkyl,
$R^2$ represents hydrogen or $C_1$–$C_4$-alkyl,
m represents 0 or 1 and
n represents 0 or 1.

$Ar^1$ particularly preferably represents phenyl which is optionally monosubstituted to tetrasubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different fluorine or chlorine substituents, $C_1$–$C_4$-alkoxy which is monosubstituted to pentasubstituted by identical or different fluorine or chlorine substituents, $SCF_3$, $SCHF_2$, nitro and cyano, or represents pyridyl, thiazolyl, imidazolyl, thienyl or pyrazolyl, each of which is optionally monosubstituted or disubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different fluorine or chlorine substituents, $C_1$–$C_4$-alkoxy which is mono-substituted to pentasubstituted by identical or different fluorine or chlorine substituents, $SCF_3$, $SCHF_2$, nitro and cyano.

$Ar^2$ particularly preferably represents phenyl which is optionally mono-substituted to pentasubstituted by identical or different substituents from the series consisting of fluorine, chlorine, bromine, $C_1$–$C_{18}$-alkyl, $C_1$–$C_6$-alkoxy-$C_1$–$C_8$-alkyl, $C_1$-$C_8$-alkoxy which is monosubstituted to hexasubstituted by identical or different fluorine or chlorine substituents, $C_1$–$C_2$-alkyl which is monosubstituted to pentasubstituted by identical or different fluorine or chlorine substituents, $C_1$–$C_{18}$-alkoxy, —$(OC_2H_4)_{1-3}$—O—$C_1$–$C_6$-alkyl, $C_1$–$C_{12}$-alkylthio, $C_1$–$C_8$-alkylthio which is monosubstituted to hexasubstituted by identical or different fluorine or chlorine substituents, cyclohexyl or cyclohexyloxy, each of which is optionally substituted by $C_1$–$C_4$-atkyl, $C_1$–$C_4$-alkoxy, cyclohexyl or phenyl, pyridyloxy which is optionally monosubstituted or disubstituted by identical or different substituents from the series consisting of fluorine, chlorine and $CF_3$, and phenyl, benzyl, phenethyl, phenoxy, phenoxymethyl, phenylthio, phenethyloxy, benzyloxy, benzylthio or styryl, each of which is optionally monosubstituted to trisubstituted by identical or different substituents from the series consisting of $C_1$–$C_{12}$-alkyl, fluorine, chlorine, bromine, cyano, $CF_3$, $C_1$–$C_4$-alkoxy, $C_1$–$C_4$-alkoxy which is monosubstituted to hexasubstituted by identical or different fluorine or chlorine substituents, $C_1$–$C_4$-alkoxy-$C_1$–$C_4$-alkyl, $C_1$–$C_4$-alkoxyethylenoxy, $C_1$–$C_4$-alkylthio, $C_1$–$C_4$-alkylthio which is monosubstituted to hexasubstituted by identical or different fluorine or chlorine substituents, and trimethylsilyl, or represents pyridyl, thiazolyl, imidazolyl, thienyl or pyrazolyl, each of which is optionally monosubstituted to trisubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different fluorine or chlorine substituents, $C_1$–$C_4$-alkoxy which is monosubstituted to pentasubstituted by identical or different fluorine or chlorine substituents, $SCF_3$, $SCHF_2$, nitro and cyano.

X particularly preferably represents the group —$(CHR^1)_m$—$(CHR^2)_n$—, in which
$R^1$ represents hydrogen or methyl,
$R^2$ represents hydrogen or methyl,
m represents 0 or 1 and
n represents 0 or 1.

$Ar^1$ very particularly preferably represents phenyl which is optionally monosubstituted to trisubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different fluorine or chlorine substituents, $C_1$–$C_4$-alkoxy which is monosubstituted to pentasubstituted by identical or different fluorine or chlorine substituents, $SCF_3$, $SCHF_2$, nitro and cyano, or represents thienyl.

$Ar^2$ very particularly preferably represents phenyl which is optionally monosubstituted to tetrasubstituted by identical or different substituents from the series consisting of fluorine, chlorine, bromine, $C_1$–$C_{18}$-alkyl, $C_1$–$C_6$-alkoxy-$C_1$–$C_8$-alkyl, $C_1$-$C_8$-alkoxy which is monosubstituted to hexasubstituted by identical or different fluorine or chlorine substituents, $C_1$–$C_2$-alkyl is monosubstituted to pentasubstituted by identical or different fluorine or chlorine substituents, $C_1$–$C_{18}$-alkoxy, —$(OC_2H_4)_{1-3}$—O—$C_1$–$C_6$-alkyl, $C_1$–$C_{12}$-alkylthio, $C_1$–$C_8$-alkylthio which is monosubstituted to hexasubstituted by identical or different fluorine or chlorine substituents, cyclohexyl or cyclohexyloxy, each of which is optionally substituted by $C_1$–$C_4$-alkyl, $C_1$–$C_4$-alkoxy, cyclohexyl or phenyl, pyridyloxy which is optionally monosubstituted or disubstituted by identical or different substituents from the series consisting of fluorine, chlorine and $CF_3$, and phenyl, benzyl, phenethyl, phenoxy, phenoxymethyl, phenylthio, phenethyloxy, benzyloxy, benzylthio or styryl, each of which is optionally monosubstituted to trisubstituted by identical or different substituents from the series consisting of $C_1$–$C_{12}$-alkyl, fluorine, chlorine, bromine, cyano, $CF_3$, $C_1$–$C_4$-alkoxy, $C_1$–$C_4$-alkoxy which is monosubstituted to hexasubstituted by identical or different fluorine or chlorine substituents, $C_1$–$C_4$-alkoxy-$C_1$–$C_4$-alkyl, $C_1$–$C_4$-alkoxyethylenoxy, $C_1$–$C_4$-alkylthio, $C_1$–$C_4$-alkylthio which is monosubstituted to hexasubstituted by identical or different fluorine or chlorine substituents, and trimethylsilyl, X very particularly preferably represents the group —(CHR$^1$)$_m$—(CHR$^2$)$_n$—, in which
  R$^1$ represents hydrogen,
  R$^2$ represents hydrogen,
  m represents 0 or 1 and
  n represents 0 or 1.
Ar$^1$ very particularly especially represents phenyl which is monosubstituted to trisubstituted by identical or different substituents from the series consisting of fluorine, chlorine, trifluoromethyl and trifluoromethoxy, or represents thienyl.

Ar$^2$ very particularly especially represents phenyl which is optionally monosubstituted to trisubstituted by identical or different substituents from the series consisting of fluorine, chlorine, bromine, $C_1$–$C_6$-alkyl, or by phenyl, phenoxy or benzyloxy, each of which is optionally monosubstituted or disubstituted by identical or different substituents from the series consisting of fluorine, chlorine, trifluoromethyl and trifluoromethoxy.

X very particularly especially represents the group —(CH$_2$)$_m$—, in which
  m is 0 or 1.

The hydrocarbon radicals such as alkyl which have been mentioned above in the definition of the compounds according to the invention are in each case straight-chain or branched as far as this is possible, also in connection with hetero atoms, such as alkoxy.

Examples of substituents Ar$^1$ and Ar$^2$ are listed in Tables 1 and 2 below:

TABLE 1

| AR$^1$ | Ar$^1$ | Ar$^1$ | Ar$^1$ | Ar$^1$ |
|---|---|---|---|---|
| 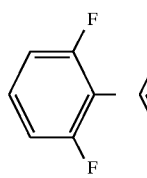 | 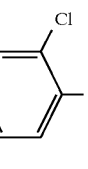 | 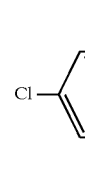 | 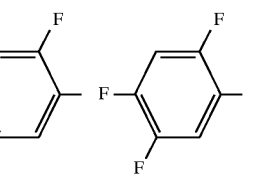 | 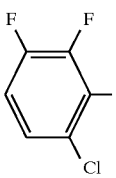 |
| 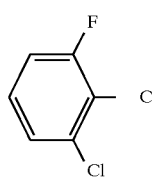 | 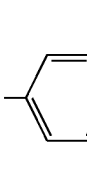 | 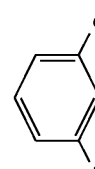 | 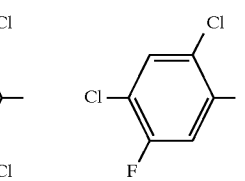 | 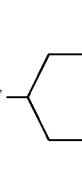 |
| 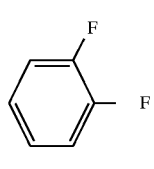 | 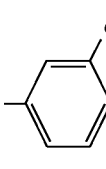 | 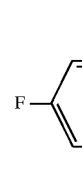 | 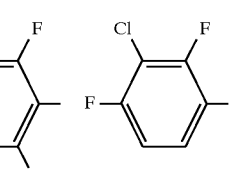 | 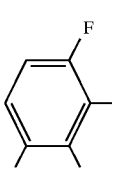 |

TABLE 2

| Ar$^2$ | Ar$^2$ | Ar$^2$ |
|---|---|---|
| 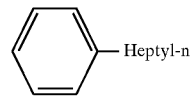 | 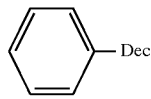 | 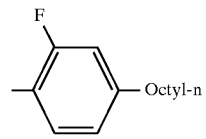 |
| 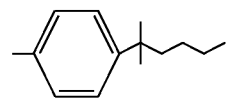 | 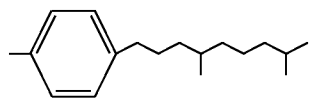 | 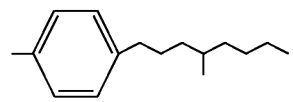 |
| 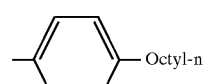 | 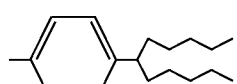 | 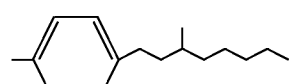 |

TABLE 2-continued

| Ar² | Ar² | Ar² |
|---|---|---|
| ⟨phenyl⟩—hexyl | ⟨phenyl⟩—Dodecyl-n | ⟨phenyl⟩—heptyl-iso |
| ⟨phenyl⟩—isopentyl | ⟨phenyl⟩—Pentadecyl-n | ⟨phenyl⟩—octyl-iso |
| ⟨phenyl, m-Nonyl-n⟩ | ⟨phenyl⟩—(sec-octyl) | ⟨phenyl, 2-F⟩—Nonyl-n |
| ⟨phenyl⟩—Nonyl-n | ⟨phenyl, 2-F⟩—Undecyl-n | ⟨phenyl⟩—O-Dodecyl-n |
| ⟨phenyl, 2-F⟩—Heptyl-n | ⟨phenyl, 2-F⟩—Tridecyl-n | ⟨phenyl⟩—O-Tridecyl-n |
| ⟨phenyl, 2-Cl⟩—Octyl-n | ⟨phenyl, 2-Decyl-n, 5-F⟩ | ⟨phenyl⟩—O-Tetradecyl-n |
| ⟨phenyl, 2-CH₃⟩—Octyl-n | ⟨phenyl, 2-Cl⟩—Heptyl-n | ⟨phenyl⟩—O-Pentadecyl-n |
| ⟨phenyl, 2-F⟩—Decyl-n | ⟨phenyl, 2-CH₃O⟩—Octyl-t | ⟨phenyl⟩—O-Hexadecyl-n |
| ⟨phenyl, 2-F⟩—Dodecyl-n | ⟨phenyl, 2-C₂H₅—O⟩—Nonyl-n | ⟨phenyl⟩—O-Heptadecyl-n |
| ⟨phenyl, 2-Cl⟩—Dodecyl-n | —CH₂—⟨phenyl⟩—Octyl-n | ⟨phenyl⟩—O-Octadecyl-n |
| ⟨phenyl, 2-CH₃O⟩—Decyl-n | ⟨phenyl⟩—O-Heptyl-n | ⟨phenyl⟩—S-Nonyl-n |

TABLE 2-continued

| Ar² | Ar² | Ar² |
|---|---|---|
| 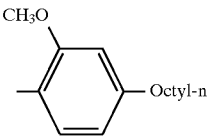 3-CH₃O, 4-Octyl-n phenyl | 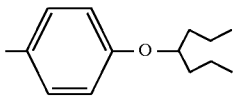 4-(O-sec-pentyl)phenyl | 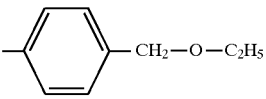 4-(CH₂—O—C₂H₅)phenyl |
| 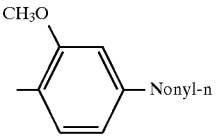 3-CH₃O, 4-Nonyl-n phenyl | 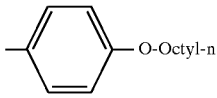 4-(O-Octyl-n)phenyl | 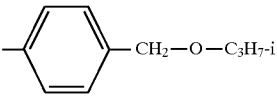 4-(CH₂—O—C₃H₇-i)phenyl |
| 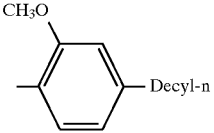 3-CH₃O, 4-Decyl-n phenyl | 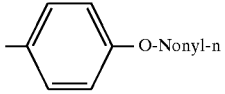 4-(O-Nonyl-n)phenyl | 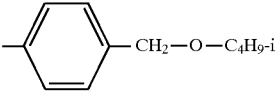 4-(CH₂—O—C₄H₉-i)phenyl |
| 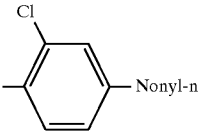 3-Cl, 4-Nonyl-n phenyl | 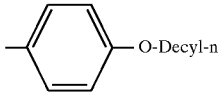 4-(O-Decyl-n)phenyl | 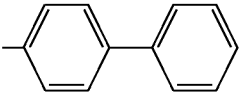 biphenyl |
| 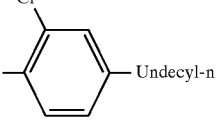 3-Cl, 4-Undecyl-n phenyl | 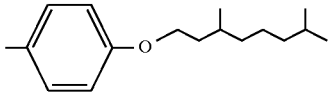 4-(O-3,7-dimethyloctyl)phenyl | 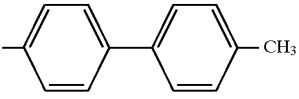 4'-CH₃-biphenyl |
| 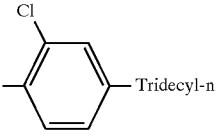 3-Cl, 4-Tridecyl-n phenyl | 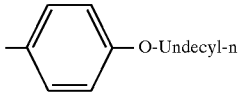 4-(O-Undecyl-n)phenyl | 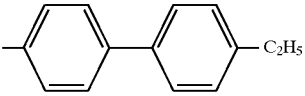 4'-C₂H₅-biphenyl |
| 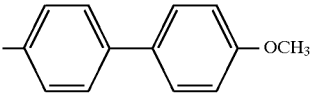 4'-OCH₃-biphenyl | 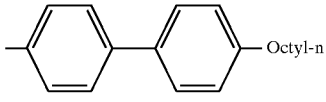 4'-Octyl-n-biphenyl | 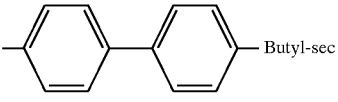 4'-Butyl-sec-biphenyl |
| 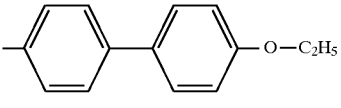 4'-O—C₂H₅-biphenyl | 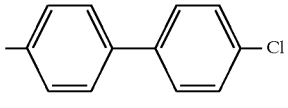 4'-Cl-biphenyl | 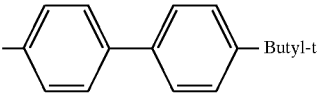 4'-Butyl-t-biphenyl |
| 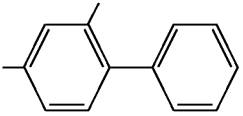 2'-F-biphenyl | 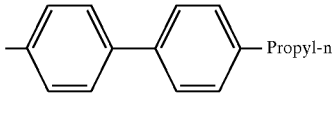 4'-Propyl-n-biphenyl | 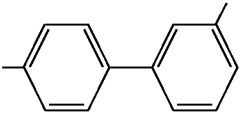 3'-Cl-biphenyl |
| 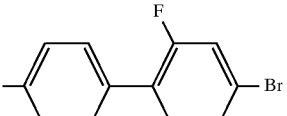 2'-F, 4'-Br-biphenyl | 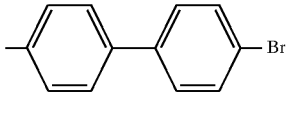 4'-Br-biphenyl | 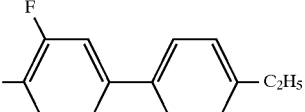 2'-F, 4'-C₂H₅-biphenyl |
| 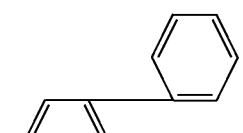 4-OCH₃, benzyl-phenyl | 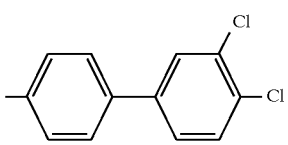 3',4'-Cl₂-biphenyl | 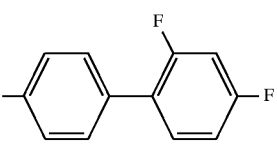 2',4'-F₂-biphenyl |

TABLE 2-continued
| Ar² | Ar² | Ar² |
|---|---|---|
| 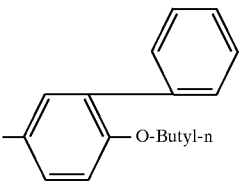 | 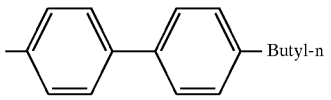 | 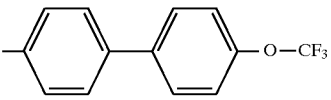 |
| 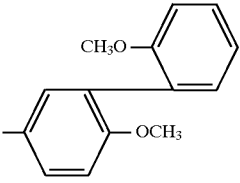 | 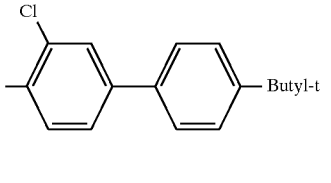 | 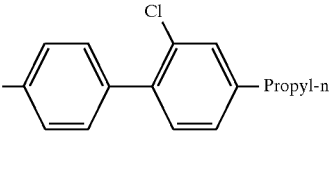 |
| 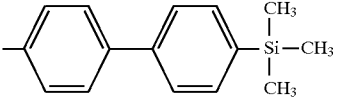 | 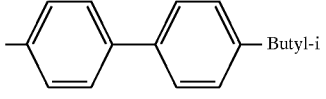 | 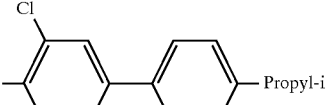 |
| 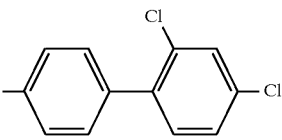 | 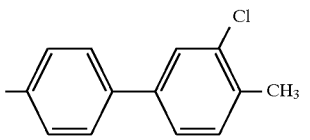 | 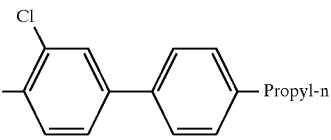 |
| 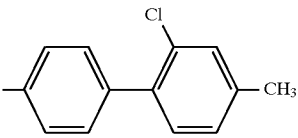 | 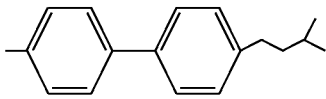 | 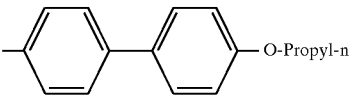 |
| 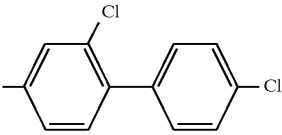 | 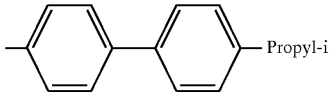 | 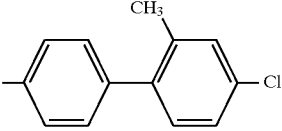 |
| 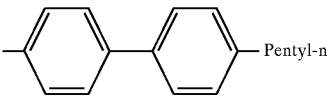 | 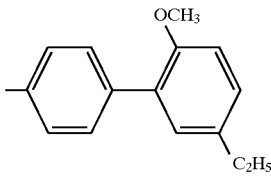 | 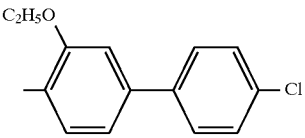 |
| 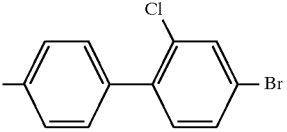 | 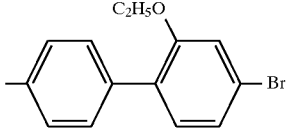 | 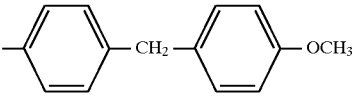 |
| 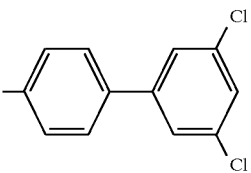 | 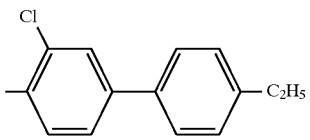 | 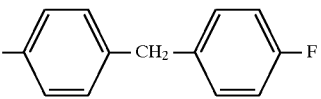 |

TABLE 2-continued
| Ar² | Ar² | Ar² |
|---|---|---|
| 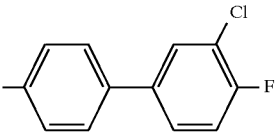 | 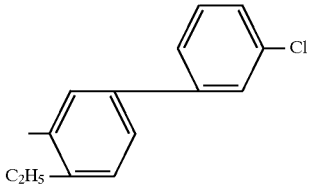 | 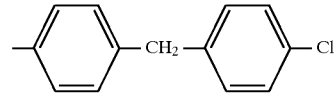 |
| 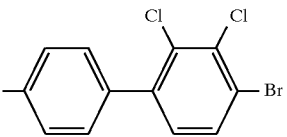 | 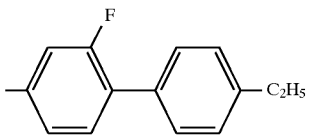 | 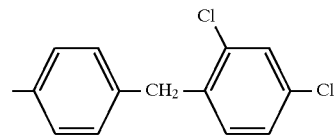 |
| 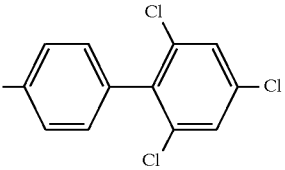 | 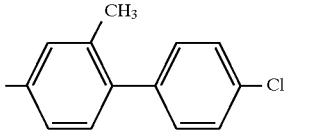 | 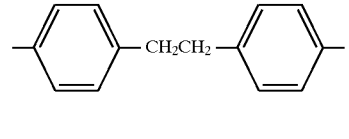 |
| 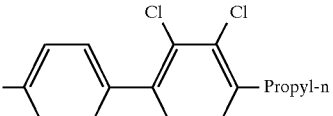 | 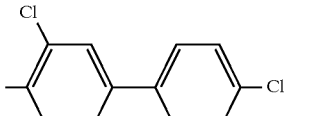 | 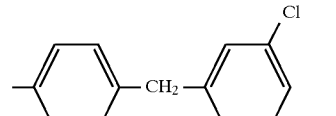 |
| 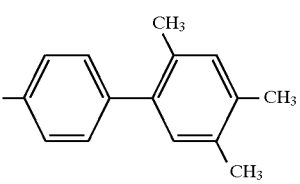 | 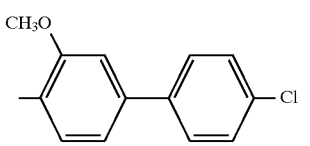 | 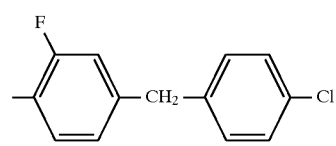 |
| 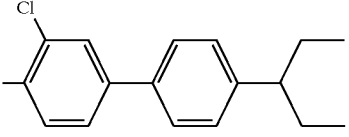 | 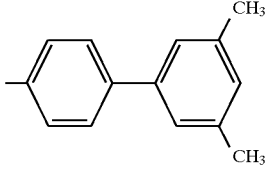 | 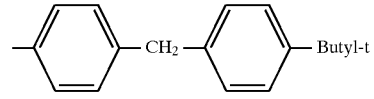 |
| 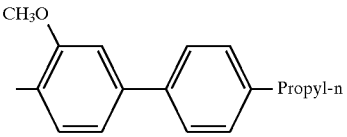 | 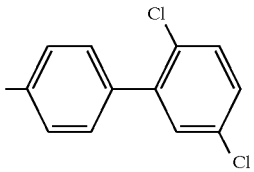 | 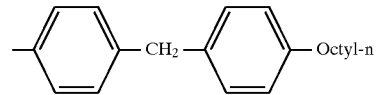 |
| 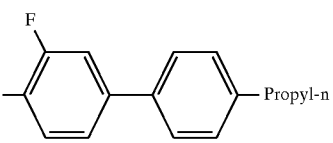 | 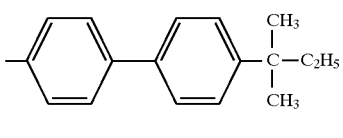 | 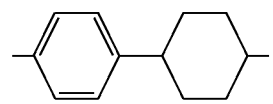 |
| 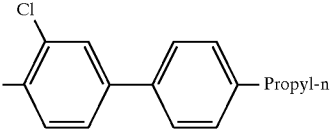 | 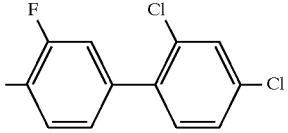 | 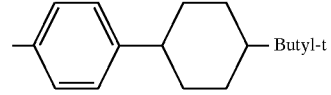 |

TABLE 2-continued
| Ar² | Ar² | Ar² |
|---|---|---|
| 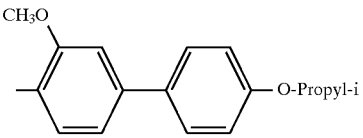 | | 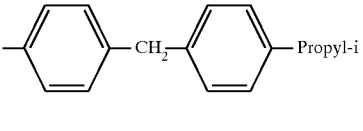 |
| 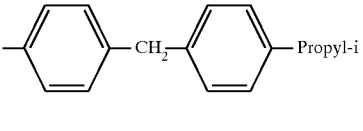 | 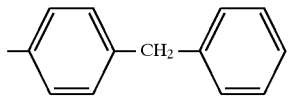 | 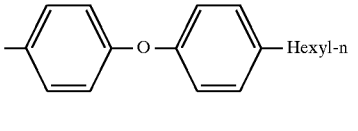 |
| 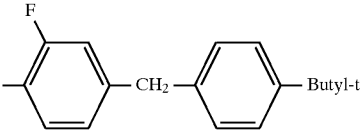 | 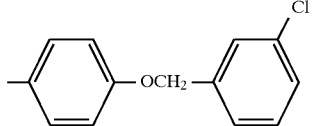 | 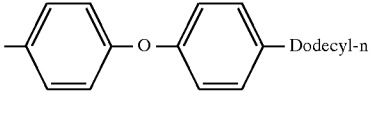 |
| 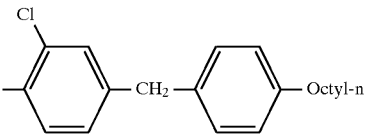 | 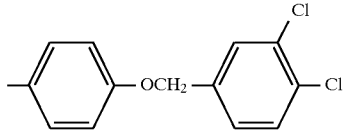 | 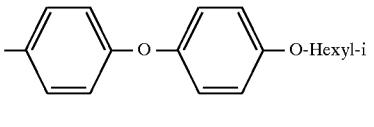 |
| 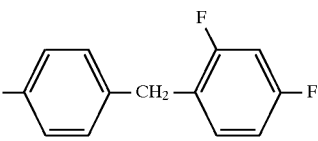 | 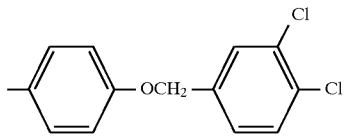 | 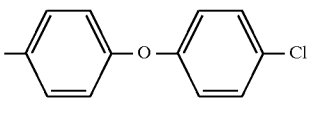 |
| 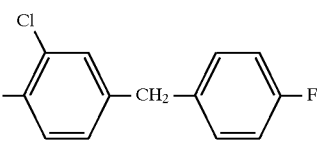 | 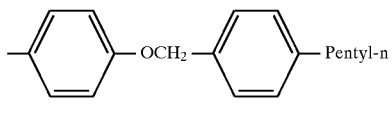 | 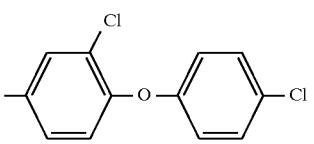 |
| 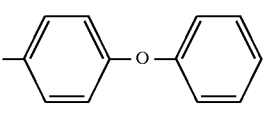 | 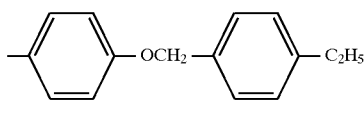 | 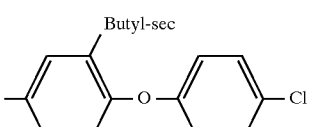 |
| 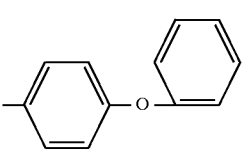 | 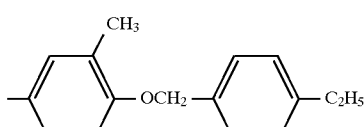 | 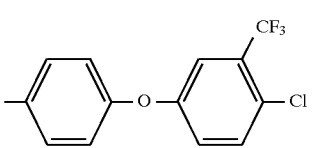 |
| 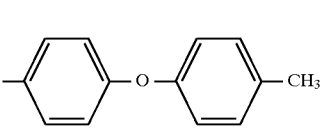 | 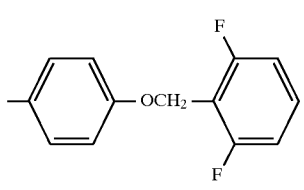 | 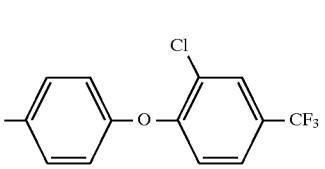 |
| 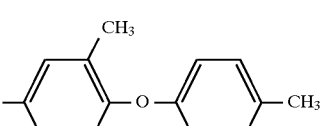 | 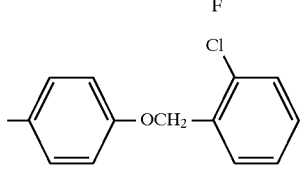 | 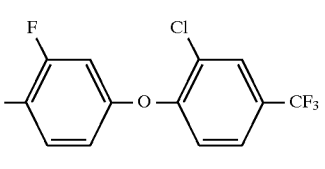 |
| 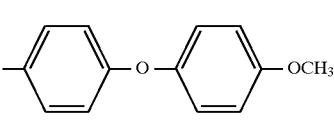 | 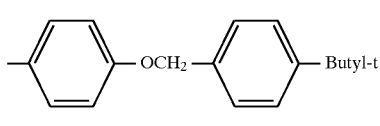 | 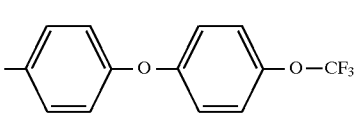 |
| | 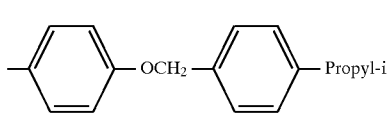 | |

TABLE 2-continued
| Ar² | Ar² | Ar² |
|---|---|---|
| 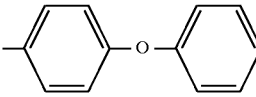 | 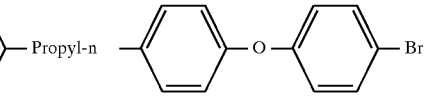 | 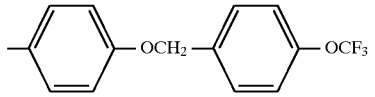 |
| 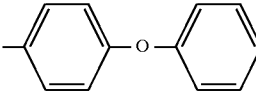 | 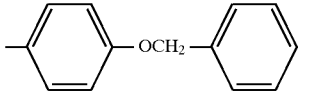 |  |
| 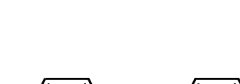 |  |  |
| 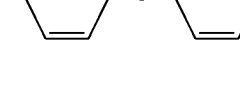 |  | 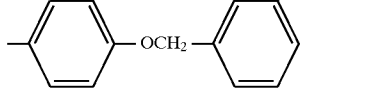 |
| 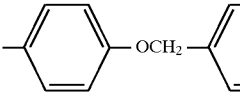 | 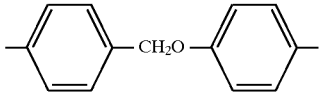 | 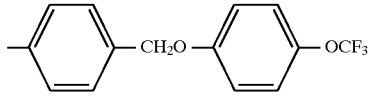 |
| 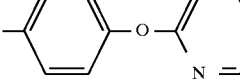 | 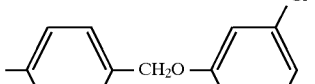 | 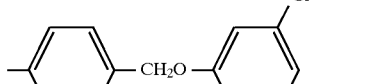 |
| 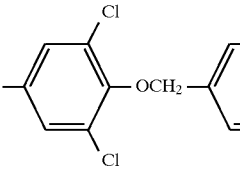 | 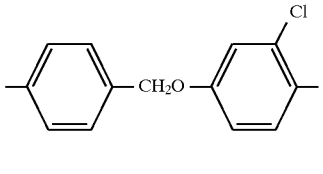 | 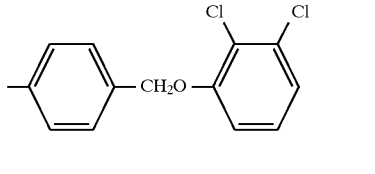 |
| 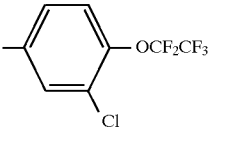 | 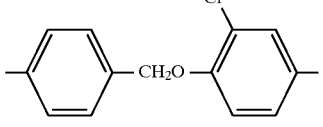 | 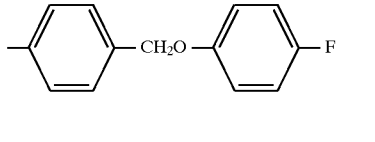 |
| 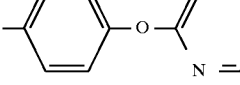 | 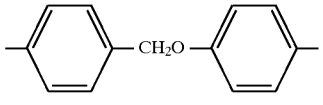 | 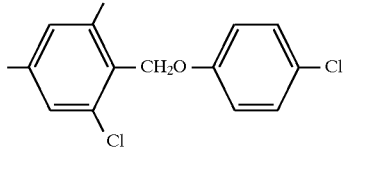 |

TABLE 2-continued

| Ar² | Ar² | Ar² |
|---|---|---|

TABLE 2-continued

| Ar² | Ar² | Ar² |
|---|---|---|
| 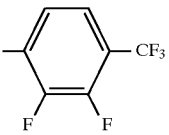 | 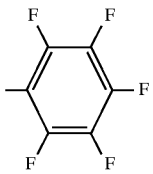 | 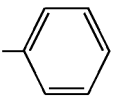 |
| 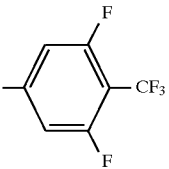 | 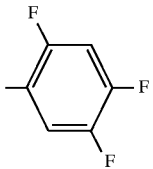 | 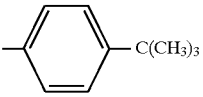 |
| 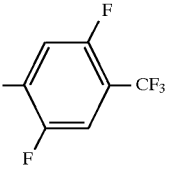 | 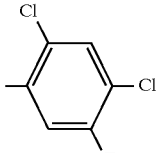 | 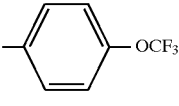 |
| | 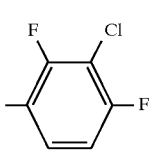 | 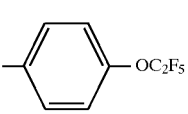 |

The abovementioned definitions of radicals or illustrations, in general or where preferred ranges have been mentioned, can be combined with each other as desired, that is to say that combinations between the respective ranges and preferred ranges are also possible. They apply to the end products and, analogously to the precursors and intermediates.

Preferred compounds of the formula (I) according to the invention are those in which there exists a combination of the meanings (preferably) mentioned above as being preferred.

Particularly preferred compounds of the formula (I) according to the invention are those in which there exists a combination of the meanings mentioned above as being particularly preferred.

Very particularly preferred compounds of the formula (I) according to the invention are those in which there exists a combination of the meanings mentioned above as being very particularly preferred.

Very particularly special compounds of the formula (I) according to the invention are those in which there exists a combination of the meanings mentioned above as being very particularly especially preferred.

If, for example, 1-(2,6-difluorobenzoyl)-2-(4-bromophenyl)-hydrazine and 1-bromo-2-fluoroethane are used as starting materials in accordance with process (a), the course of the process according to the invention can be represented by the following equation:

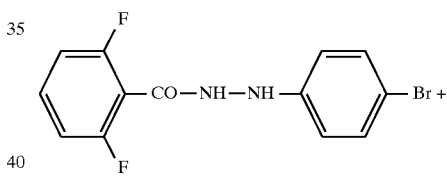

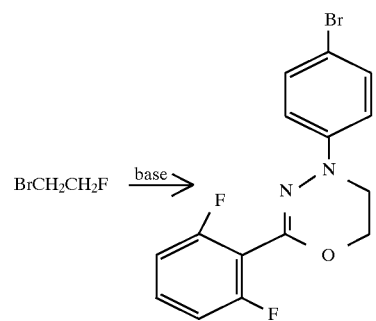

If, for example, 1-(2,6-difluorobenzoyl)-2-(2,4,6-trichlorophenyl)-2-(2-bromoeth-1-yl)-hydrazine is used as starting material and, if appropriate, potassium iodide as the catalyst in accordance with process (b), the course of the process according to the invention can be represented by the following equation:

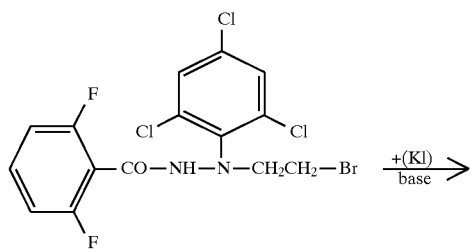

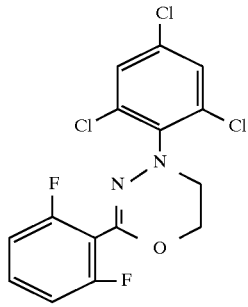

If, for example, 1-(2,6-difluorobenzoyl)-2-(2,4,6-trichlorophenyl)-2-(2-hydroxyeth-1-yl)hydrazine is used as starting material in accordance with process (c), the course of the process according to the invention can be represented by the following equation:

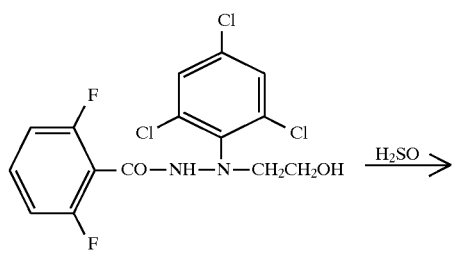

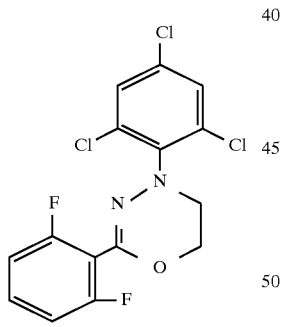

If, for example, 1-(2,6-difluorophenyl)-4H-5,6-dihydro-1,3,4-oxadiazine and benzyl bromide are used as starting materials in accordance with process (d), the course of the process according to the invention can be represented by the following equation:

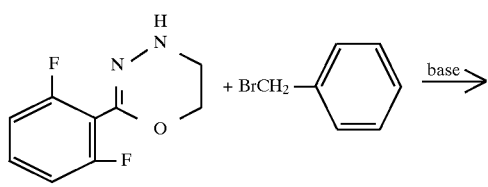

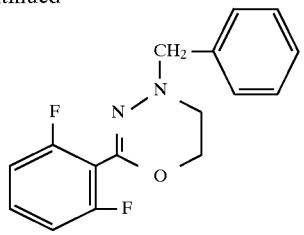

If, for example, 2-(2,6-difluorophenyl)-4-(4-bromophenyl-4H-5,6-dihydro-1,3,4-oxadiazine and 4-trifluoromethoxyphenylboronic acid are used as starting materials in accordance with process (e), the course of the process according to the invention can be represented by the following equation:

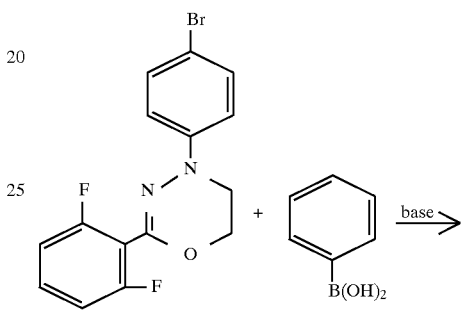

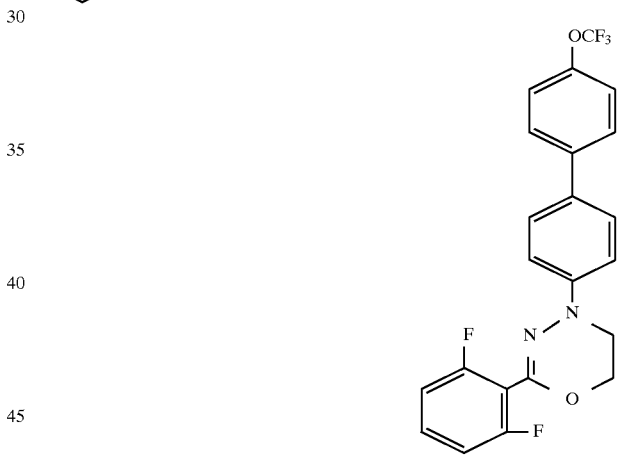

Formula (II) provides a general definition of the acid hydrazides required as starting materials for carrying out process (a) according to the invention.

The acid hydrazides of the formula (II) are known or can be obtained in a generally known manner (cf. in this context, for example, U.S. Pat. No. 2 167 793; Revue Roumaine de Chimie 29 (2), 219–22 (1984); Liebigs Annalen der Chemie 1975, 1264). Acid hydrazides of the formula (II) are obtained for example when acid hydrazides of the formula (IX)

$$Ar^1-CO-NH-NH_2 \qquad (IX)$$

in which
 $Ar^1$ has the abovementioned meanings,
are reacted with aldehydes of the formula (X)

$$Ar^1-X-CHO \qquad (X)$$

in which

Ar² and X have the abovementioned meanings, but where at least one of the indices m and n represents 0, in the presence of a diluent, for example aromatic hydrocarbons or alcohols, such as, for example, toluene or ethanol, and if appropriate in the presence of a condensing agent, for example an acid, such as, for example, p-toluenesulphonic acid, at temperatures between 20° and 120° C. (cf. also Farmaco Ed. Sci. 39 (1984), 414 and the Preparation Examples);

and the resulting acylidene derivatives of the formula (XI)

Ar¹—CO—NH—N=CH—X—Ar²  (X)

in which

Ar¹, Ar² and X have the abovementioned meanings are reduced, for example using hydrogen in the presence of a catalyst (for example palladium/charcoal) or using borohydrides (for example sodium borohydride or calcium borohydride) if appropriate in the presence of a diluent, for example alcohols such as methanol or ethanol, at temperatures between 0° and 100° C. and if appropriate under elevated pressure (cf. also Liebigs Annalen der Chemie 1975, 1264; Farmaco Ed. Sci. 16 (1961) 832 and the Preparation Examples);

or when active carboxylic acid derivatives, for example of the formulae (XIIa–c)

Ar¹—CO—Cl  (XIIa)

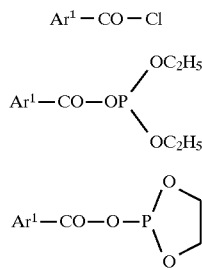

(XIIb)

(XIIc)

in which

Ar¹ has the abovementioned meanings are reacted with hydrazines of the formula (XIII)

Ar²—X—NH—NH₂  (XIII)

in which

Ar² and X have the abovementioned meanings are reacted in the presence of a diluent, for example, optionally halogenated aliphatic or aromatic hydrocarbons such as, for example, methylene chloride or toluene, and if appropriate in the presence of a base, for example organic nitrogen bases such as, for example triethylamine, at temperatures between 0° and 100° C. (cf. also U.S. Pat. No. 2 617 793; Revue Roumaine de Chimie 29 (2), 219–22 (1984)).

The acid hydrazides of the formula (IX), the aldehydes of the formula (X), the carboxylic acid derivatives of the formula (XIIa–c) and the hydrazines of the formula (XIII) are known (cf., for example, the abovementioned references) or can be obtained in a generally known manner.

Formula (III) provides a general definition of the ethane derivatives furthermore required as starting materials for carrying out process (a) according to the invention. In formula (III), Y¹ and Y² are identical or different and represent generally customary leaving groups, such as halogen, in particular fluorine, chlorine or bromine, alkylsulphonyloxy, in particular methylsulphonyloxy, or optionally substituted arylsulphonyloxy, in particular phenylsulphonyloxy, p-chlorophenylsulphonyloxy or tolylsulphonyloxy.

The ethane derivatives of the formula (III) are generally known compounds of organic chemistry.

Formula (IV) provides a general definition of the acid hydrazides required as starting materials for carrying out the process (b) according to the invention. Y² represents one of the leaving groups which have already been mentioned above in connection with the description of the ethane derivatives of the formula (III).

The acid hydrazides of the formula (IV) occur as intermediates when carrying out process (a) according to the invention and can be isolated. They can also be obtained by converting the leaving group Z in the acid hydrazides of formula (V), into the leaving group Y² in a generally known manner.

Formula (V) provides a general definition of the acid hydrazides required as starting materials for carrying out the process (c) according to the invention. Z preferably represents one of the leaving groups hydroxyl or —O—CO—R, where R preferably represents C₁–C₄-alkyl, in particular methyl.

The acid hydrazides of the formula (V) are obtained, for example, by reacting acid hydrazides of the formula (II) with known ethane derivatives of the formula (IIIa)

Y¹—CH₂—CH₂—Z  (IIIa)

in which

Y¹ and Z have the abovementioned meanings in accordance with the conditions of process (a) according to the invention.

Formula (VI) provides a general definition of the 1,3,4-oxadiazine derivatives required as starting materials for carrying out the process (d) according to the invention.

The 1,3,4-oxadiazine derivatives of the formula (VI) are known (cf., for example, Pesticide Science 1993, 38, 309–314; Pesticide Biochemistry and Physiology 47, 1–7 (1993)) or can be obtained by the processes described in these publications.

Formula (VII) provides a general definition of the compounds furthermore required as starting materials for carrying out process (d) according to the invention.

The compounds of the formula (VII) are generally known compounds of organic chemistry.

Formula (Ia) provides a general definition of the 1,3,4-oxadiazine derivatives required as starting materials for carrying out process (e) according to the invention.

Ar³ preferably represents iodo- or bromophenyl, particularly preferably 4-iodo- or 4-bromophenyl.

The 1,3,4-oxadiazine derivatives of the formula (Ia) are compounds according to the invention and can be obtained in accordance with processes (a) to (d) according to the invention.

Formula (VIII) provides a general definition of the boronic acids furthermore required as starting materials for carrying out process (e) according to the invention. In formula (VIII), Ar⁴ preferably represents phenyl which is optionally monosubstituted to trisubstituted by identical or different substituents from the series consisting of C₁–C₁₂-alkyl, halogen, cyano, C₁–C₄-halogenoalkyl, C₁–C₆-alkoxy, C₁–C₆-halogenoalkoxy, C₁–C₆-alkoxy-C₁–C₆-alkyl, C₁–C₆-alkoxy-ethylenoxy, C₁–C₆-alkylthio, C₁–C₆-halogenoalkylthio and trimethylsilyl, particularly preferably phenyl which is optionally monosubstituted to trisubstituted by identical or different substituents from the series consisting of $C_1$–$C_{12}$-alkyl, fluorine, chlorine, bromine, cyano, $CF_3$, $C_1$-$C_4$-alkoxy, $C_1$-$C_4$-alkoxy which is monosubstituted to hexasubstituted by identical or different fluorine or chlorine substituents, $C_1$–$C_4$-alkoxy-$C_1$–$C_4$-alkyl, $C_1$–$C_4$-alkoxyethylenoxy, $C_1$–$C_4$-alkylthio, $C_1$-$C_4$-alkylthio which is monosubstituted to hexasubstituted by identical or different fluorine or chlorine substituents or trimethylsilyl, and particularly preferably phenyl which is optionally substituted by trifluoromethyl or trifluoromethoxy.

The boronic acids of the formula (VIII) are generally known compounds of organic chemistry.

Diluents which are suitable for carrying out processes (a) to (e) according to the invention are all organic solvents which are inert under the reaction conditions in question. If appropriate, they can be used in the form of a mixture of water. Substances which are preferably used are hydrocarbons, such as toluene, xylene, tetralin, hexane, cyclohexane, halogenohydrocarbons such as methylene chloride, chloroform, chlorobenzene, o-dichlorobenzene, alcohols such as methanol, ethanol, glycol, the isomeric propanols, butanols, pentanols, ethers such as diethyl ether, diisopropyl ether, dimethoxyethane, tetrahydrofuran, dioxane, nitriles such as acetonitrile or butyronitrile, amides such as dimethylformamide, sulphoxides such as dimethyl sulphoxide, and furthermore sulpholane.

Suitable bases for carrying out the processes (a), (b), (d) and (e) according to the invention are all customary acid acceptors. The following can preferably be used: tertiary amines, such as triethylamine, pyridine, diazabicyclooctane (DABCO), diazabicycloundecene (DBU), diazabicyclononene (DBN), N,N-dimethylaniline, furthermore alkaline earth metal oxides, such as magnesium oxide or calcium oxide, in addition alkali metal carbonates and alkaline earth metal carbonates, such as sodium carbonate, potassium carbonate or calcium carbonate, alkali metal hydroxides, such as sodium hydroxide or potassium hydroxide, and furthermore alcoholates, such as sodium ethanolate or potassium tert-butylate.

If appropriate, process (b) according to the invention is carried out in the presence of a catalyst. Examples of suitable catalysts are: potassium iodide, pyridine or DABCO.

Process (c) according to the invention is carried out in the presence of an acid. In principle, inorganic or organic acids are suitable. Acids which are preferably used are, for example, sulphuric acid, methanesulphonic acid, benzenesulphonic acid or p-toluenesulphonic acid.

When carrying out processes (a) to (e) according to the invention, the reaction temperatures can be varied within a substantial range. In general, the processes are carried out at temperatures between 0° C. and 150° C., preferably between 0° C. and 100° C., or at the boiling point of the solvent used.

In general, processes (a) to (e) according to the invention are carried out under atmospheric pressure; however, if appropriate, it is also possible to carry out the processes under elevated pressure.

Processes (a) to (e) according to the invention are generally carried out using equimolar amounts of reactants, 0.01 to 0.1 mol of catalyst, 0.5 to 1.0 mol of acid and 1 to 10 mol of base being employed, if appropriate. Working-up is carried out by customary methods.

The active compounds are suitable for combating animal pests, preferably arthropods, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Macrosiphum avenae, Myzus spp., Pemphigus spp., Phorodon humuli, Phylloxera vastatrix, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajutus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp.,*

*Niptus hololeucus, Gibbium psylloides, Tribolium spp., Tenebrio molitor, Agriotes spp., Conoderus spp., Melolontha melolontha, Arnphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the order of Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp.,Bryobia praetiosa, Panonychus spp.* and *Tetranychus spp.*

The active compounds according to the invention are distinguished by high insecticidal and acaricidal activity.

They can be employed particularly successfully for combating phytopathogenic mites, such as, for example, against the two-spotted spider mite (*Tetranychus urticae*).

The active compounds can be converted into the customary formulations, such as solutions, emulsions, suspensions, powders, dusting compositions, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is, liquid solvents, and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, aryl-sulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Particularly advantageous components in mixtures are, for example, the following:

Fungicides:

2-aminobutane; 2-anitino-4-methyl-6-cyclopropyl-pyrimidine; 2', 6'-dibromo-2-methyl-4'-trifluoromethoxy-4'-trifluoro-methyl-1,3-thiazole-5-carboxanilide; 2,6-dichloro-N-(4-trifluorometliylbenzyl)benzamide; (E)-2-methoxyimino-N-methyl-2-(2-phenoxy-phenyl)acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methox-imino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusutfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulfur arid sulfur preparations, tebuconazole, tecloftalam, tecnazene, tetraconazole, thiabendazole, thicyofen, thiophanate-methyl, tlhiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chorophenyl)-1-(ethoxymethyl)-5-(trifluoromethyl)-1-H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chloretoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators is also possible.

The active compound according to the invention can furthermore be present in its commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.00001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

Preparation and use of the active compounds according to the invention can be seen from the examples which follow.

Preparation Examples

Example 1

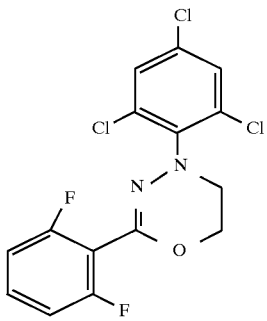

(Process a)

1.75 g (5.0 mmol) of 2-(2,6-difluorobenzoyl)-1-(2,4,6-trichlorophenyl)-hydrazine and 1.38 g (10.0 mmol) of potassium carbonate are stirred for 20 minutes at room temperature in 4 ml of dimethylacetamide. After 0.94 g (5.0 mmol) of dibrornomethane have been added, the mixture is stirred overnight at 90° C. The reaction mixture is added to ethyl acetate/water, and the organic phase is dried over sodium sulphate and concentrated in vacuo. The residue is chromatographed on silica get 60 (ethyl acetate/hexane (1:3)). This gives 0.48 g (25% of theory) of 2-(2,6-difluorophenyl) -4-(2,4,6-trichlorophenyl)-4H-5,6-dihydro-1,3,4-oxadiazine of melting point 107°–108° C.

Example 2

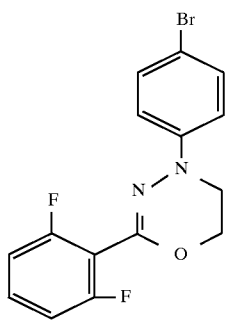

(Process a)

2.50 g (62.5 mmol) of sodium hydroxide in 8 ml of water are added dropwise at room temperature to a mixture of 9.81 g (30.0 mmol) of 1-(2,6-difluorobenzoyl)-2-(4-bromophenyl)-hydrazine and 3.81 g (30.0 mmol) of 1-bromo-2-fluoroethane in 70 ml of absolute ethanol. After the mixture has been stirred for 5 hours, it is heated at 60° C. for a further 5 hours. The cooled solution is partitioned between methyl tert-butyl ether and water, and the organic phase is separated off and dried over sodium sulphate. After column chromatography (silica gel 60; ethyl acetate/hexane 1:3), 1.60 g (15% of theory) of 4-(4-bromophenyl)-2-(2,6-difluorophenyl)-4H-5,6-dihydro-1,3,4-oxadiazine of melting point 138°–140° C. are obtained.

Example 3

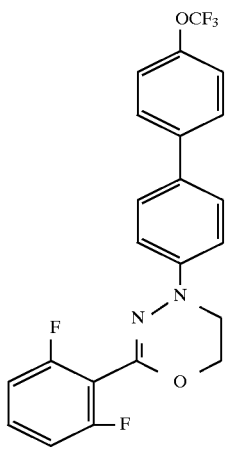

(Process e)

0.70 g (2.0 mmol) of 4-(4-bromophenyl)-2-(2,6-difluorophenyl)-4H-5,6-dihydro-1,3,4-oxadiazine (Ex. 2) and 0.42 g (2.0 mmol) of water-moist 4-trifluoromethoxyphenylboronic acid are stirred overnight at 100° C. with 2.7 g (20 mmol) of ground potassium carbonate in 6 ml of toluene/water/ethanol (2:1:1). After cooling, the reaction mixture is diluted with ethyl acetate, and the organic phase is separated off. It is dried over sodium sulphate and then concentrated in vacuo. The residue is taken up in hot ethyl acetate and the product is precipitated using hexane. This gives 0.8 g (93% of theory) of 4-[4-(4-trifluoromethoxyphenyl)phenyl]-2-(2,6-difluorophenyl)-4H-5,6-dihydro-1,3,4-oxadiazine of melting point 130°–133° C.

Example 4

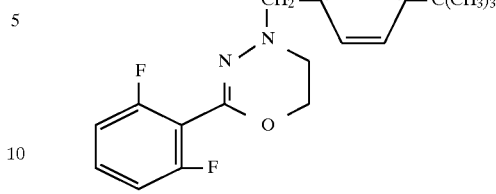

(Process a)

5.0 g (39.4 mmol) of 1,2-bromofluoroethane are added at room temperature to a solution of 12.0 g (37.7 mmol) of 2-(4-tert-butylbenzyl)-2,6-difluorobenzohydrazide in 50 ml of ethanol. A solution of 3.2 g (80 mmol) of sodium hydroxide in 20 ml of water is added dropwise to this mixture, and the batch is refluxed for 18 hours. Filtration with suction and drying of the resulting white precipitate yields 4.8 g (37% of theory) of 2-(2,6-difluorophenyl)-4-(4-tert-butylbenzyl)-4H-5,6-dihydro-1,3,4-oxadiazine of melting point 62°–64° C.

PREPARATION OF THE STARTING MATERIAL

Example (II1)

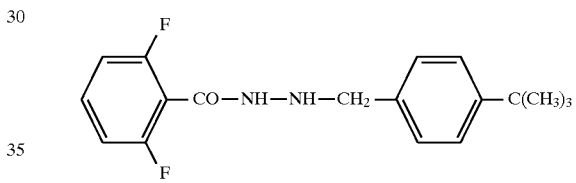

15.8 g (50 mmol) of 2-(4-tert-butylphenyl)methylene-2,6-difluorobenzohydrazide are dissolved in 120 ml of ethanol, 1 g of 10% palladium/charcoal is added, and the mixture is then hydrogenated for 8 hours at 3 bar and room temperature. The pale yellow oil obtained after the catalyst has been filtered off and the solvent removed is chromatographed on silica gel (ethyl acetate/hexane 1:4). This gives 11.4 g (72% of theory) of 2-(4-tert-butylbenzyl)-2,6-difluorobenzohydrazide as a colourless oil.

Example (XI-1)

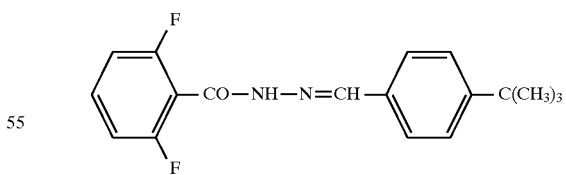

9.0 g (53 mmol) of 2,6-difluorobenzohydrazide and 8.6 g (53 mmol) of 4-tert-butylbenzaldehyde are dissolved in 150 ml of toluene and refluxed for 16 hours on a water separator. Removal of the solvent under reduced pressure yields 16.5 g (98% of theory) of 2-(4-tert-butylphenyl)methylene-2,6-difluorobenzohydrazide as a yellowish oil which is further reacted directly.

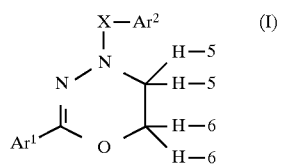
| Ex. No. | Ar¹ | X | Ar² | Physical constants M.p. (°C.) or δ (¹H NMR) in DMSO or log p*⁾ |
|---|---|---|---|---|
| 5 | 2,6-diF-phenyl | — | 4-Cl-phenyl | M.p. 122° C. |
| 6 | 2-F-6-Cl-phenyl | — | 4-Cl-phenyl | M.p. 86° C. |
| 7 | 2,6-diF-phenyl | — | 3,5-diCl-phenyl | H-5: 3.95 t (triplet)<br>H-6: 4.59 t |
| 8 | 2,6-diF-phenyl | — | 4-C(CH₃)₃-phenyl | H-5: 3.63 t<br>H-6: 4.59 t |
| 9 | 2-F-6-Cl-phenyl | — | 3,5-diCl-phenyl | H-5: 3.95 t<br>H-6: 4.59 t |
| 10 | 2,6-diF-phenyl | — | phenyl | H-5: 3.84 t<br>H-6: 4.58 t |
| 11 | 2-F-6-Cl-phenyl | — | 2,4,6-triCl-phenyl | H-5: 3.65 t<br>H-6: 4.60 t |

-continued

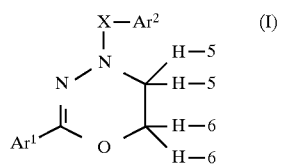

| Ex. No. | Ar¹ | X | Ar² | Physical constants M.p. (°C.) or δ (¹H NMR) in DMSO or log p*⁾ |
|---|---|---|---|---|
| 12 | 2,6-difluorophenyl | — | 3-bromophenyl | H-5: 3.88 t<br>H-6: 4.58 t |
| 13 | 2,6-difluorophenyl | — | 3-(4-trifluoromethoxyphenyl)phenyl | H-5: 3.89 t<br>H-6: 4.62 t |
| 14 | 4-chlorophenyl | —CH₂— | 4-bromophenyl | M.p. 115° C. |
| 15 | 4-chlorophenyl | —CH₂— | 4'-trifluoromethylbiphenyl-4-yl | M.p. 169° C. |
| 16 | 4-trifluoromethylphenyl | —CH₂— | 4-(4-methoxyphenoxy)phenyl | M.p. 90° C. |
| 17 | 4-trifluoromethoxyphenyl | —CH₂— | biphenyl-4-yl | M.p. >200° C. |
| 18 | 2,4-dichlorophenyl | —CH₂— | 4-phenoxyphenyl | log p (pH 2) = 5.61 |
| 19 | 2,5-dichlorophenyl | —CH₂— | 4-(2-chloro-4-trifluoromethylphenoxy)phenyl | log p (pH 2) = 6.35 |
| 20 | 2-thienyl | —CH₂— | 4-bromophenyl | log p (pH 2) = 4.26 |

-continued

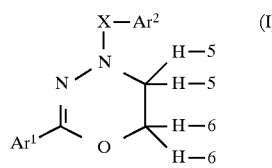

| Ex. No. | Ar¹ | X | Ar² | Physical constants M.p. (°C.) or δ (¹H NMR) in DMSO or log p*⁾ |
|---|---|---|---|---|
| 21 | 2,6-difluorophenyl | −CH₂− | 2,6-dichloro-4-(4-chlorobenzyloxy)phenyl | log p (pH 2) = 5.67 |
| 22 | 2,6-difluorophenyl | −CH₂− | 4-bromophenyl | log p (pH 2) = 4.03 |
| 23 | 2-thienyl | −CH₂− | 4'-(trifluoromethoxy)biphenyl-4-yl | log p (pH 2) = 5.41 |
| 24 | 2-thienyl | −CH₂− | 2,6-dichloro-4-(4-chlorobenzyloxy)phenyl | log p (pH 2) = 5.95 |
| 25 | 2,5-dichlorophenyl | −CH₂− | 3-phenoxyphenyl | log p (pH 2) = 5.57 |
| 26 | 4-(trifluoromethyl)phenyl | −CH₂− | 4-(2-chloro-4-trifluoromethylphenoxy)phenyl | log p (pH 2) = 6.44 |
| 27 | 3,4-dichlorophenyl | −CH₂− | 4-fluoro-3-phenoxyphenyl | log p (pH 2) = 6.13 |
| 28 | 2-thienyl | −CH₂− | 4'-(trifluoromethyl)biphenyl-4-yl | M.p. 150° C. |

-continued

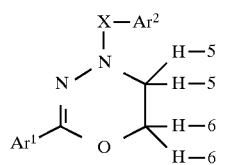

| Ex. No. | Ar¹ | X | Ar² | Physical constants M.p. (°C.) or δ (¹H NMR) in DMSO or log p*⁾ |
|---|---|---|---|---|
| 29 | 2,6-difluorophenyl | —CH₂— | 4'-(trifluoromethoxy)biphenyl-4-yl | log p (pH 2) = 5.15 |
| 30 | 2,6-difluorophenyl | —CH₂— | biphenyl-4-yl | log p (pH 2) = 4.49 |
| 31 | 3-(trifluoromethyl)phenyl | —CH₂— | 4-[2-chloro-4-(trifluoromethyl)phenoxy]phenyl | log p (pH 2) = 6.43 |
| 32 | 4-fluorophenyl | —CH₂— | 4-bromophenyl | log p (pH 2) = 4.73 |
| 33 | 2,5-dichlorophenyl | —CH₂— | 4-fluoro-3-phenoxyphenyl | log p (pH 2) = 5.41 |
| 34 | 3,5-dichlorophenyl | —CH₂— | 4-bromophenyl | log p (pH 2) = 6.47 |
| 35 | 3-fluorophenyl | —CH₂— | 4-bromophenyl | log p (pH 2) = 4.80 |
| 36 | 3-fluorophenyl | —CH₂— | 4'-(trifluoromethoxy)biphenyl-4-yl | log p (pH 2) = 5.87 |

-continued

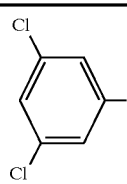

| Ex. No. | Ar¹ | X | Ar² | Physical constants M.p. (°C.) or δ (¹H NMR) in DMSO or log p*⁾ |
|---|---|---|---|---|
| 37 | 3,5-dichlorophenyl | —CH$_2$— | 4'-OCF$_3$-biphenyl | log p (pH 2) = 7.36 |
| 38 | 2,6-difluorophenyl | —CH$_2$— | phenyl | log p (pH 2) = 3.38 | are obtained analogously to Preparation Examples 1 to 4 or in accordance with the general preparation instructions.

Use Examples

In the Use Example which follows, compound (A) which is known from Pesticide Biochemistry and Physiology 47, 1–7 (1993), is employed as comparison substance:

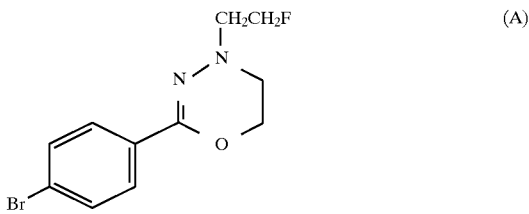

2-(4-Bromophenyl)-4-(2-fluoroeth-1-yl)-4H-5,6-dihydro-1,3,4-oxadiazine.

Example
Tetranychus-Test (OP resistant/spray treatment)
Solvent: 3 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentrations.

Bean plants (Phaseolus vulgaris) which are severely infested with all stages of the two-spotted spider mite (*Teiranychus urticae*) are sprayed with a preparation of active compound of the desired concentration.

After the desired time, the action is determined in %. 100% means that all spider mites have been destroyed; 0% means that no spider mites have been destroyed.

In this test, for example the compounds of Preparation Examples 3 and 4 brought about a destruction of 95% and 98%, respectively, after 5 days at an exemplary active compound concentration of 0.001%, while the known compound (A) showed no action.

We claim:

1. Compounds of the formula (I)

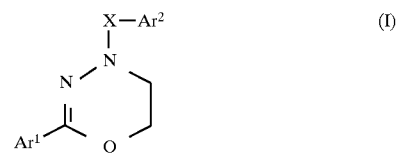

in which

Ar¹ represents phenyl which is monosubstituted to trisubstituted by identical or different substituents selected from the group consisting of fluorine, chlorine, trifluoromethyl and trifluoromethoxy, or represents thienyl, Ar² represents phenyl which is optionally monosubstituted to trisubstituted by identical or different substituents selected from the group consisting of fluorine, chlorine, bromine, $C_1$–$C_6$-alkyl, or by phenyl, phenoxy or benzyloxy, each of which is optionally monosubstituted or disubstituted by identical or different substituents selected from the group consisting of fluorine, chlorine, trifluoromethyl and trifluoromethoxy, X represents the group —$(CH_2)_m$—, in which m is 0 or 1.

2. A pesticidal composition comprising an amount of a compound according to claim 1 effective for combatting insects and arachnids and a diluent.

3. A method of combating insects and arachnids which comprises administering to such insects and arachnids or to a locus from which it is desired to exclude such insects and arachnids an amount of a compound according to claim 1 effective for combatting said insects and arachnids.

* * * * *